(12) United States Patent
Agami et al.

(10) Patent No.: US 7,572,641 B2
(45) Date of Patent: Aug. 11, 2009

(54) PHARMACEUTICAL COMPOSITIONS COMPRISING MELOXICAM AND METHODS OF THEIR PREPARATION

(75) Inventors: Michal Agami, Netanya (IL); Julia Hrakovsky, Rosh Ha-Ayin (IL); Ruth Tenengauzer, Hod Hasharon (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 470 days.

(21) Appl. No.: 11/286,184

(22) Filed: Nov. 22, 2005

(65) Prior Publication Data

US 2007/0116760 A1    May 24, 2007

(51) Int. Cl.
*G01N 1/00*    (2006.01)
(52) U.S. Cl. .................. 436/174; 514/937; 514/951; 514/960; 436/518; 436/74
(58) Field of Classification Search ............. 436/174, 436/518, 74
See application file for complete search history.

(56) References Cited

FOREIGN PATENT DOCUMENTS

DE    102 50 081    5/2004
EP    0 945 134    9/1999

OTHER PUBLICATIONS

Li, Shoufeng, et al., IV-IVC Consideration in the Development of Immediate-Release Oral Dosage Form, Jul. 2005, Journal of Pharmaceutical Sciences, vol. 94(7), p. 1396-1417.*
Odman, J.A.L., et al, The effect of particle size on in vitro dissolution and bioavailability of a low solubility drug, [online], [retrievd on Jun. 26, 2008] Retrieved from the internet <URL:http://www.aapspharmsci.org/abstracts/AM_1999/1843.htm>.*
Time stamp of Odman, [online], [retrievd on Jun. 26, 2008] Retrieved from the internet <URL:http://www.aapspharmsci.org/abstracts/AM_1999/>.*
Boehringer Ingelheim Internatonal GmbH, Mobic Medicaton Guide, 2004, NDA 20-938/S-004.*
Dressman, Jennifer B., In Vitro-in vivo correlaton for lipophilic, poorly water-soluble drugs, 2000, European Journal of Pharmaceutical Sciences, vol. 11 supplemental 2, pp. s73-s80.*
Watkins, "Fighting the Clock: Pharmaceutical and biotechnology companies seek ways to reduce the time required to discover and develop medicines", *Chemical and Engineering News*, p. 27-34 (Jan. 28, 2002).
United States Pharmacopeia, USP 28/NF23, pp. 2412-15 (2005).
United States Pharmacopeia, USP 28/NF23, pp. 2645 (2005).
Physician's Desk Reference, PDR 58 ed. p. 1016-1019 (Thomson PDR 2004).

* cited by examiner

*Primary Examiner*—Yelena G Gakh
*Assistant Examiner*—Robert Xu
(74) *Attorney, Agent, or Firm*—Kenyon & Kenyon LLP

(57) ABSTRACT

The present invention encompasses a method of evaluating pharmaceutical compositions of meloxicam whereby one can correlate in vitro properties to in vivo properties, and pharmaceutical compositions developed using the method.

21 Claims, No Drawings

PHARMACEUTICAL COMPOSITIONS COMPRISING MELOXICAM AND METHODS OF THEIR PREPARATION

FIELD OF THE INVENTION

This invention encompasses pharmaceutical compositions of meloxicam, methods of their preparation, and methods of correlating their pharmacokinetic properties to in vitro properties.

BACKGROUND OF THE INVENTION

Meloxicam is a member of the enolic acid group of non-steroidal anti-inflammatory drugs ("NSAIDs"). Its chemical name is 4-hydroxy-2-methyl-N-(5-methyl-2-thiazolyl)-2H-1,2-benzothiazine-3-carboxamide 1,1-dioxide and it has a molecular weight of 351.4. Meloxicam has the following structural formula:

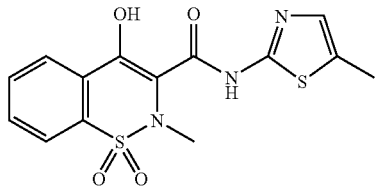

Meloxicam is a NSAID that exhibits anti-inflammatory, analgesic, and antipyretic activities in animal models. Meloxicam is approved for use in the United States and is sold as Mobic® Tablets in 7.5 mg and 15 mg forms for oral administration. See *Physicians' Desk Reference*, p. 1016 (Thomson P D R 2004). It has also been produced as an oral suspension in a 7.5 mg dosage form.

In the pharmaceutical field, much effort and expense is invested in developing new pharmaceutical formulations. See, e.g., Karen J. Watkins, "Fighting the Clock: Pharmaceutical and biotechnology companies seek ways to reduce the time required to discover and develop medicines", *Chemical and Engineering News*, p. 27 (Jan. 28, 2002). Much of the expense stems from the necessity of performing biological studies to assure safety, efficacy, and bioequivalence prior to marketing the drug. It is estimated that it takes approximately 12 years and costs approximately $800 million to bring a drug from conception to the marketplace. Id.

Over the years, pharmaceutical companies have constantly been searching for ways to reduce the enormous amounts of time and money required to develop a new drug, without compromising quality. The present invention provide methods of drug development that will reduce costs, maximize profits, and/or allow companies to get new, high-quality drugs to the public sooner.

SUMMARY OF THE INVENTION

One embodiment of the invention encompasses a method for selecting a solid meloxicam pharmaceutical formulation comprising providing at least one pharmaceutical formulation comprising meloxicam particles, dissolving in vitro the pharmaceutical formulation, determining the amount by weight of meloxicam dissolved in about 15 minutes, comparing the amount by weight of meloxicam dissolved from the pharmaceutical formulation to the amount by weight of meloxicam dissolved from a reference pharmaceutical formulation, and selecting the pharmaceutical formulation having the amount of dissolved meloxicam comparable to the amount of dissolved meloxicam of the reference pharmaceutical formulation.

The dissolving step of the method is performed by dissolving the pharmaceutical formulation using an U.S.P. Dissolution Apparatus 2 filled with a dissolution medium of 1000 ml of 0.01M $KH_2PO_4$ aqueous solution at a pH of about 7.5; adding the solid meloxicam pharmaceutical formulation to the dissolution medium at about 37° C. and a rotation speed of about 75 rpm; and measuring the dissolved meloxicam as a percent by weight at regular intervals. In one embodiment, the regular intervals are 15-minute intervals.

One embodiment of the invention encompasses a method for selecting a solid meloxicam pharmaceutical formulation having the pharmacokinetic parameter $C_{max}$. $C_{max}$ may be from about 1200 ng/ml to about 1500 ng/ml when dosed at 15 mg to healthy volunteers. Preferably, $C_{max}$ is from about 1215 ng/ml to about 1488 ng/ml when dosed at 15 mg to healthy volunteers. The solid meloxicam pharmaceutical formulation may have a mean $AUC_\infty$ in addition to $C_{max}$. The mean $AUC_\infty$ may be from about 39000 ng*hr/ml to about 61000 ng*hr/ml when dosed at 15 mg to healthy volunteers. Preferably, the mean $AUC_\infty$ is from about 39082 ng*hr/ml to about 60588 ng*hr/ml when dosed at 15 mg to healthy volunteers.

One embodiment of the invention encompasses the method described above, wherein the pharmaceutical formulations comprise particles of meloxicam ranging in size from about 4 microns to about 370 microns. The particles may have a $d_{(0.5)}$ from about 20 microns to about 55 microns and a $d_{(0.9)}$ less than about 90 microns. In an alternative embodiment, the invention encompasses the method described above, wherein the pharmaceutical formulations comprise particles of meloxicam having $d_{(0.9)}$ less than about 90 microns or $d_{(0.5)}$ from about 20 microns to about 55 microns.

One embodiment of the invention encompasses a pharmaceutical composition comprising a solid meloxicam pharmaceutical formulation selected by the method described above having particles of meloxicam or a salt thereof, wherein the particle size of meloxicam or a salt thereof is from about 4 microns to about 370 microns, $d_{(0.5)}$ is from about 20 microns to about 55 microns, and $d_{(0.9)}$ is less than about 90 microns, between 60% and 85% by weight of meloxicam dissolves within about 15 minutes, when dissolved using an U.S.P. Dissolution Apparatus 2 (paddle apparatus) filled with a dissolution medium of 1000 ml of 0.01M $KH_2PO_4$ aqueous solution at a pH of about 7.5 at about 37° C. and a rotation speed of about 75 rpm, and the mean $C_{max}$ in the fasting state is from about 1200 ng/ml to about 1500 ng/ml when dosed at 15 mg to healthy volunteers. Preferably, $C_{max}$ is from about 1215 ng/ml to about 1488 ng/ml when dosed at 15 mg to healthy volunteers. The pharmaceutical composition may have a mean $AUC_\infty$ in addition to $C_{max}$. The mean $AUC_\infty$ may be from about 39000 ng*hr/ml to about 61000 ng*hr/ml when dosed at 15 mg to healthy volunteers. Preferably, the mean $AUC_\infty$ is from about 39082 ng*hr/ml to about 60588 ng*hr/ml when dosed at 15 mg to healthy volunteers. In an alternative embodiment, the pharmaceutical composition is in the form of a tablet or capsule. The meloxicam or salt thereof may be present in the pharmaceutical composition in an amount of about 5 mg to about 30 mg. The pharmaceutical composition may further comprise at least one of lactose, cellulose, sodium citrate dihydrate, povidone, crospovidone, silicon dioxide, and magnesium stearate.

DETAILED DESCRIPTION OF THE INVENTION

The rising costs of drug development can be reduced if pharmaceutical companies evaluate new pharmaceutical compositions by using a method that correlates in vitro studies to in vivo studies. The method of the invention intends to decrease the expense involved in developing pharmaceutical compositions by correlating pharmacological properties of a composition with the in vitro properties. Not to be limited by theory, but it is believed that the method will reduce development time and avoid and/or reduce extensive biological testing. The present invention encompasses a method of evaluating pharmaceutical compositions of meloxicam whereby one can correlate in vitro properties to in vivo properties. With the method one can predict the in vivo pharmacokinetic data of a meloxicam pharmaceutical composition by measuring the in vitro dissolution data of the composition and comparing it to the in vitro dissolution data of a reference composition with known in vivo pharmacokinetic properties.

As used herein unless otherwise defined, the term "in vivo pharmacokinetic data" means pharmacokinetic data of a drug within the body. Such data includes, but is not limited to, AUC, $AUC_\infty$ (log-transformed) $C_{max}$, $T_{max}$, and $T_{1/2}$.

As used herein unless otherwise defined, the term "reference tablet" or "reference pharmaceutical formulation" means a commercially available tablet of meloxicam. Preferably, the reference tablet is manufactured by Boehringer Ingelheim.

The method of the invention correlates in vitro dissolution data with in vivo pharmacokinetic data to determine the in vivo effect of a particular formulation. Preferably, the formulation is in the form of a solid such as a tablet or capsules. The method comprises providing at least one pharmaceutical formulation comprising meloxicam particles, dissolving in vitro the pharmaceutical formulation, determining the amount by weight of meloxicam dissolved over time, comparing the amount by weight of meloxicam dissolved from the pharmaceutical formulation to the amount of meloxicam dissolved from a reference pharmaceutical formulation, and selecting the pharmaceutical formulation having dissolved meloxicam comparable to dissolved meloxicam of the reference meloxicam pharmaceutical formulation. Typically, the dissolving time is about 15 minutes. If after about 15 minutes, the dissolved percentage of meloxicam by weight in a pharmaceutical formulation is comparable to that of a reference pharmaceutical formulation, then the $C_{max}$ for the pharmaceutical formulation and the reference pharmaceutical formulation are similar. As used in this context, "comparable" means that the dissolved percentage by weight of meloxicam in the pharmaceutical formulation and the reference pharmaceutical formulation does not vary by more than 20%. Thus, the percentage dissolution may vary up to a margin of error of 20% and still have the desired effect.

The dissolving step typically comprises dissolving a solid meloxicam pharmaceutical formulation using an U.S.P. Dissolution Apparatus 2 (paddle apparatus) as described in the U.S.P. See *United States Pharmacopeia*, pp. 2412-15 (U.S. Pharmacopeial Convention, Inc., 28th ed., 2005). For example, the dissolution apparatus 2 is filled with a dissolution medium of 1000 ml of 0.01M $KH_2PO_4$ aqueous solution at a pH of about 7.5. Then the pharmaceutical formulation is added to the dissolution medium and the dissolved meloxicam as a percent by weight is measured at regular intervals in the apparatus at 37° C. Preferably, the percentage of meloxicam by weight dissolved in the apparatus is measured at 15-minute intervals between 0 and 60 minutes.

The solid meloxicam pharmaceutical formulation may be in the form of a tablet. Typically, the tablet is made from particles of meloxicam ranging in size from about 4 microns to about 370 microns. Preferably, $d_{(0.5)}$ ranges from about 20 microns to about 165 microns, and more preferably, $d_{(0.5)}$ ranges from about 20 microns to about 55 microns. And preferably, $d_{(0.9)}$ is less than about 90 microns. The particle size is measured using a Mastersizer S modular particle size analyzer (manufactured by Malvern Instruments) and a dissolution medium of 0.065% w/v dioctyl sulfosuccinate sodium salt in n-hexane. For example, a typical measurement comprises suspending about 0.05 g to 0.07 g of meloxicam in about 5 ml of the dissolution medium followed by mixing and sonication for about 15 seconds. Thereafter, the suspension is added into the flow cell filled with recirculating dilution medium to achieve an obscuration in the range of 15% to 35%. Table 1 summarizes several tablets made with different particle size distributions.

TABLE 1

| Particle size of meloxicam samples | | | |
|---|---|---|---|
| Sample # | $d_{(0.1)}$ | $d_{(0.5)}$ | $d_{(0.9)}$ |
| I |  | 4 | 8 |
| II | 3 | 14 | 32 |
| III | 10 | 65 | 170 |
| IV | 0.3 | 1 | 4 |
| V | 19 | 99 | 165 |
| VI | 37 | 166 | 363 |
| VII |  | 32 | 57 |

In Table 1, $d_{(0.1)}$ is the particle size, in microns, below which 10% by volume distribution of the population is found, $d_{(0.5)}$ is the particle size, in microns, below which 50% by volume distribution of the population is found, and $d_{(0.9)}$ is the particle size, in microns, below which 90% by volume distribution of the population is found.

Preferably, the tablet is made from particles of meloxicam and at least one commercially available pharmaceutical excipient commonly known to the skilled artisan. Excipients include, but are not limited to, at least one of lactose, cellulose, sodium citrate dihydrate, povidone PVP K-30, crospovidone, colloidal silicon dioxide, or magnesium stearate. Preferably, the tablet contains between 7.5 mg and 15 mg of meloxicam.

The pharmacokinetic parameters of interest include, but are not limited to, AUC, $AUC_\infty$ (log-transformed) $C_{max}$, $T_{max}$, and $T_{1/2}$. Typically, the desired $C_{max}$ ranges from an amount of about 2391 ng/ml to 1194 ng/ml. Preferably, the $C_{max}$ ranges from about 1926 ng/ml to 1194 ng/ml. More preferably, the $C_{max}$ ranges from about 1500 ng/ml to about 1200 ng/ml, and most preferably, the $C_{max}$ ranges from about 1488 ng/ml to about 1215 ng/ml. Typically, the desired $AUC_\infty$ ranges from about 78417 ng*hr/ml to about 38819 ng*hr/ml. Preferably, the $AUC_\infty$ ranges from about 73725 ng*hr/ml to about 38819 ng*hr/ml. More preferably, the $AUC_\infty$ ranges from about 61000 ng*hr/ml to about 39000 ng*hr/ml, and most preferably, the $AUC_\infty$ ranges from about 60588 ng*hr/ml to about 39082 ng*hr/ml.

The invention encompasses also a pharmaceutical composition comprising meloxicam or a salt thereof, wherein between 60% and 85% by weight of the meloxicam dissolves within about 15 minutes, and the average $C_{max}$ in the fasting state is about 1215 ng/ml to 1488 ng/ml. Alternatively, between 9 and 12.75 mg of meloxicam dissolves from a 15 mg dose within about 15 minutes. The pharmaceutical composition may be in the form of a tablet or capsule. Typically, $d_{(0.5)}$ is from about 20 microns to about 55 microns, and $d_{(0.9)}$ is less than about 90 microns.

The amount of meloxicam within the pharmaceutical composition may be about 5 mg to about 30 mg. Preferably, the amount of meloxicam is about 7.5 mg to about 15 mg.

The pharmaceutical composition may further comprise excipients. Excipients include, but are not limited to, at least one of lactose, cellulose, sodium citrate dihydrate, povidone, crospovidone, silicon dioxide, or magnesium stearate. The method for dissolving the pharmaceutical composition is described above.

The invention is further defined by reference to the following examples describing in detail the methods of testing. It will be apparent to those skilled in the art that many modifications, both to materials and methods, may be practiced without departing from the scope of the invention.

EXAMPLES

Example 1

Meloxicam Samples

Several samples of meloxicam comprising different particle sizes were prepared. The particle size of the samples was measured using a Mastersizer S modular particle size analyzer (manufactured by Malvern Instruments). The dissolution medium was 0.065% w/v dioctyl sulfosuccinate sodium salt in n-hexane. About 0.05-0.07 g of meloxicam was suspended in about 5 ml of dissolution medium by mixing and sonication for about 15 seconds. The suspension was then added into the flow cell filled with recirculating dilution medium until an obscuration in the range of 15-35% was achieved. Table 2 summarizes the prepared samples of meloxicam.

TABLE 2

Particle size of meloxicam samples

| Sample # | $d_{(0.1)}$ | $d_{(0.5)}$ | $d_{(0.9)}$ |
|---|---|---|---|
| I | | 4 | 8 |
| II | 3 | 14 | 32 |
| III | 10 | 65 | 170 |
| IV | 0.3 | 1 | 4 |
| V | 19 | 99 | 165 |
| VI | 37 | 166 | 363 |
| VII | | 32 | 57 |

In Table 2, $d_{(0.1)}$ is the particle size, in microns, below which 10% by volume distribution of the population is found, $d_{(0.5)}$ is the particle size, in microns, below which 50% by volume distribution of the population is found, and $d_{(0.9)}$ is the particle size, in microns, below which 90% by volume distribution of the population is found.

Example 2

Preparation of Tablets Using Samples of Meloxicam

Tablets were prepared by combining the excipients listed in Table 3 with each of the samples of meloxicam (samples I-VII) listed in Table 2.

TABLE 3

Composition of meloxicam test tablets

| Ingredient | 7.5 mg tablet | 15 mg tablet |
|---|---|---|
| Meloxicam | 7.5 | 15.0 |
| Lactose | 77.2 | 69.7 |
| Cellulose | 56.0 | 56.0 |
| Sodium Citrate Dihydrate | 18.0 | 18.0 |
| Povidone PVP K-30 | 6.0 | 6.0 |
| Crospovidone | 12.0 | 12.0 |
| Colloidal Silicon Dioxide | 1.5 | 1.5 |
| Magnesium Stearate | 1.8 | 1.8 |

A blend was prepared by mixing lactose monohydrate, meloxicam, microcrystalline cellulose, sodium citrate dihydrate, povidone, and crospovidone in a high shear mixer. Granulation liquid was added to the blend and was mixed. The granulate was then dried in a fluid bed drier. Colloidal silicon dioxide was added to the dried granulate and mixed. The dried granulate was milled and blended in a diffusion blender. Magnesium stearate was then sieved onto the dried granulate, and mixed again. The granulate was pressed into tablets.

Example 3

In Vitro Dissolution of Meloxicam Tablets

The dissolution profile of meloxicam tablets prepared according to Example 2 were compared to commercially available tablets. Samples I-VII, and reference tablets I-IV (produced by Boehringer Ingelheim) were analyzed using the following method. An U.S.P. Dissolution Apparatus 2 (paddle apparatus) was filled with 1000 ml of dissolution medium (0.01M $KH_2PO_4$ aqueous solution at a pH of 7.5). Six tablets from each sample were dissolved in the apparatus. The rotation speed was 75 rpm and the temperature of the medium was 37° C. Samples were analyzed at 0, 15, 30, 45, and 60 minutes. The average dissolution profile for each sample is summarized below in Table 4.

TABLE 4

In vitro dissolution data for meloxicam test and reference tablets

| | Percent dissolution | | | |
|---|---|---|---|---|
| Tablet | 15 min. | 30 min. | 45 min. | 60 min. |
| Reference tablet I | 67 | 89 | 93 | 96 |
| Reference tablet II | 78 | 88 | 91 | 93 |
| Reference tablet III | 80 | 87 | 90 | 91 |
| Reference tablet IV | 81 | 93 | 95 | 95 |
| Test tablet I | 89 | 96 | 97 | 98 |
| Test tablet II | 96.6 | 104.5 | 105.7 | 106.1 |
| Test tablet III | 54 | 73.6 | 83.4 | 89.8 |
| Test tablet IV | 97.7 | 100.9 | 101.3 | 101.5 |
| Test tablet V | 50.2 | 66.1 | 75.3 | 81.2 |
| Test tablet VI | 44.5 | 60 | 69.8 | 77 |
| Test tablet VII | 72 | 91 | 95 | 97 |

Reference tablets I and II were the commercially available Boehringer Ingelheim's Mobec® (Germany), reference tablet III was Boehringer Ingelheim's Mobicox® (Canada), and reference tablet IV was Boehringer Ingelheim's Mobic® (United States). Test tablets I-VII are tablets prepared from meloxicam samples I-VII respectively.

Table 3 illustrates that the dissolution profiles of the meloxicam tablets are related to the particle sizes of meloxicam used in the formulations. Furthermore, the data illustrates that test tablet VII had a dissolution profile similar to that of reference tablets I-IV.

Example 4

Biological Studies of Meloxicam Tablets

Healthy volunteers (24) were administered two 15 mg tablets of Test Tablet I, prepared as in Example 2 using Sample I. The skilled artisan recognizes that the term "healthy volunteer" is generally defined in *United States Pharmacopeia*, p. 2645 (U.S. Pharmacopeial Convention, Inc., 28$^{th}$ ed., 2005). Sample I had a $d_{(0.5)}$ of about 4 microns. The same volunteers were also administered two 15 mg tablets of Reference Tablet I, with a wash-out period between the two administrations. Both administrations were in the fasting state. Plasma samples were taken at intervals. Samples were taken at 0, 1, 2, 3, 4, 5, 6, 7, 8, 9, 10, 12, 14, 24, 48, 72, and 96 hours. The mean $C_{max}$ and $AUC_\infty$ (log-transformed) were determined with respect to the test and reference tablets and are listed in Table 5.

TABLE 5

In vivo pharmacokinetic data for Test Tablet I and Reference Tablet I

| | Mean AUC$_\infty$ (ng * hr/ml) | Mean C$_{max}$ (ng/ml) |
|---|---|---|
| Test Tablet I | 78417 | 2391 |
| Reference Tablet I | 73725 | 1926 |
| Test tablet I/Reference tablet I | 1.06 | 1.24 |
| 90% Confidence Interval | 1.00-1.13 | 1.16-1.33 |

Example 5

Biological Studies of Meloxicam Tablets

Healthy volunteers (21) were administered one 15 mg tablet of Test Tablet VII, prepared as in Example 2 using Sample VII. Sample VII had a $d_{(0.5)}$ of about 32 microns. The same volunteers were also administered one 15 mg tablet of Reference Tablet II, with a wash-out period between the two administrations. Both administrations were in the fasting state. Plasma samples were taken at regular intervals. Samples were taken at 0, 1, 2, 3, 3.5, 4, 4.5, 5, 5.5, 6, 7, 8, 10, 12, 14, 16, 18, 24, 48, 72, and 96 hours. The mean $C_{max}$ and $AUC_\infty$ (log-transformed) were determined with respect to the test and reference tablets and are listed in Table 6.

TABLE 6

In vivo pharmacokinetic data for Test Tablet VII and Reference Tablet II

| | Mean AUC$_\infty$ (ng * hr/ml) | Mean C$_{max}$ (ng/ml) |
|---|---|---|
| Test Tablet VII | 39082 | 1215 |
| Reference Tablet II | 38819 | 1194 |
| Test tablet VII/Reference Tablet II | 0.9983 | 1.01 |
| 90% Confidence Interval | 0.95-1.05 | 0.95-1.08 |

Example 6

Biological Studies of Meloxicam Tablets

Healthy volunteers (25) were administered one 15 mg tablet of Test Tablet VII, prepared as in Example 2 using Sample VII. Sample VII had a $d_{(0.5)}$ of about 32 microns. The same volunteers were also administered one 15 mg tablet of Reference Tablet III, with a wash-out period between the two administrations. Both administrations were in the fasting state. Plasma samples were taken at regular intervals. Samples were taken at 0, 1, 2, 3, 3.5, 4, 4.5, 5, 6, 8, 10, 12, 14, 16, 20, 24, 48, 72, and 96 hours. The mean $C_{max}$ and $AUC_\infty$ (log-transformed) were determined with respect to the test and reference tablets and are listed in Table 7.

TABLE 7

In vivo pharmacokinetic data for Test Tablet VII and Reference Tablet III

| | Mean AUC$_\infty$ (ng * hr/ml) | Mean C$_{max}$ (ng/ml) |
|---|---|---|
| Test Tablet VII | 60588 | 1488 |
| Reference Tablet III | 60790 | 1576 |
| Test tablet VII/Reference tablet III | 1.00 | 0.93 |
| 90% Confidence Interval | 0.96-1.05 | 0.87-1.00 |

Example 7

Biological Studies of Meloxicam Tablets

Healthy volunteers (28) were administered one 15 mg tablet of Test Tablet VII, prepared as in Example 2 using Sample VII. Sample VII had a $d_{(0.5)}$ of about 32 microns. The same volunteers were also administered one 15 mg tablet of Reference Tablet IV, with a wash-out period between the two administrations. Both administrations were in the fasting state. Plasma samples were taken at regular intervals. Samples were taken at 0, 1, 2, 2.5, 3, 3.5, 4, 4.5, 5, 6, 8, 10, 12, 14, 16, 24, 48, 72, and 96 hours. The mean $C_{max}$ and $AUC_\infty$ (log-transformed) were determined with respect to the test and reference tablets and are listed in Table 8.

TABLE 8

In vivo pharmacokinetic data for Test Tablet VII and Reference Tablet IV

| | Mean AUC$_\infty$ (ng * hr/ml) | Mean C$_{max}$ (ng/ml) |
|---|---|---|
| Test Tablet VII | 46890 | 1462 |
| Reference Tablet III | 44820 | 1450 |
| Test tablet VII/Reference tablet III | 1.05 | 1.01 |
| 90% Confidence Interval | 1.00-1.10 | 0.94-1.08 |

What is claimed is:

1. A method of identifying a solid meloxicam pharmaceutical formulation having comparable in vivo pharmacokinetic parameters to a reference meloxicam pharmaceutical formulation by in vitro analysis comprising:

providing at least one pharmaceutical formulation comprising meloxicam particles;

dissolving in vitro the pharmaceutical formulation using an U.S.P. Dissolution Apparatus 2 (paddle apparatus) filled with a dissolution medium of 1000 ml of 0.01M KH$_2$PO$_4$ aqueous solution at a pH of about 7.5 at about 37° C. and a rotation speed of about 75 rpm;

dissolving in vitro the reference meloxicam pharmaceutical formulation using an U.S.P. Dissolution Apparatus 2 (paddle apparatus) filled with a dissolution medium of 1000 ml of 0.01M KH$_2$PO$_4$ aqueous solution at a pH of about 7.5 at about 37° C. and a rotation speed of about 75 rpm;

determining the amount by weight of meloxicam dissolved from the reference meloxicam pharmaceutical formulation and the amount by weight of meloxicam dissolved from the meloxicam pharmaceutical formulation after about 15 minutes from starting the dissolution of each formulation;

comparing the amount by weight of meloxicam dissolved from the pharmaceutical formulation to the amount of meloxicam dissolved from the reference pharmaceutical formulation; and identifying the pharmaceutical formulation having the amount of dissolved meloxicam comparable to the amount of dissolved meloxicam of the reference pharmaceutical formulation.

2. The method according to claim 1, wherein the pharmacokinetic parameter is $C_{max}$.

3. The method according to claim 2, wherein the mean $C_{max}$ is from about 1200 ng/ml to about 1500 ng/ml when dosed at 15 mg to healthy volunteers.

4. The method according to claim 3, wherein the mean $C_{max}$ is from about 1215 ng/ml to about 1488 ng/ml when dosed at 15 mg to healthy volunteers.

5. The method according to claim 3, wherein the pharmaceutical formulation has a mean $AUC_{\infty}$ from about 39000 ng*hr/ml to about 61000 ng*hr/ml when dosed at 15 mg to healthy volunteers.

6. The method according to claim 5, wherein the pharmaceutical formulation has a mean $AUC_{\infty}$ from about 39082 ng*hr/ml to about 60588 ng*hr/ml when dosed at 15 mg to healthy volunteers.

7. The method according to claim 1, wherein the meloxicam particles have a $d_{(0.5)}$ from about 20 microns to about 55 microns and a $d_{(0.9)}$ less than about 90 microns.

8. The method according to claim 1, wherein the pharmaceutical formulation has meloxicam particles having a $d_{(0.9)}$ less than about 90 microns.

9. The method according to claim 1, wherein the pharmaceutical formulation has meloxicam particles having a $d_{(0.5)}$ from about 20 microns to about 55 microns.

10. The method according to claim 1, wherein the pharmaceutical formulation has meloxicam particles having sizes from about 4 microns to about 370 microns.

11. A pharmaceutical composition comprising a pharmaceutical formulation identified according to the method of claim 1 having particles of meloxicam or a salt thereof, wherein the particle size of meloxicam or a salt thereof is from about 4 microns to about 370 microns, $d_{(0.5)}$ is from about 20 microns to about 55 microns, and $d_{(0.9)}$ is less than about 90 microns;

between 60% and 85% by weight of meloxicam dissolves within about 15 minutes after starting dissolution of the pharmaceutical formulation when dissolved using an U.S.P. Dissolution Apparatus 2 (paddle apparatus) filled with a dissolution medium of 1000 ml of 0.01M $KH_2PO_4$ aqueous solution at a pH of about 7.5 at about 37° C. and a rotation speed of about 75 mm; and the mean $C_{max}$ in the fasting state is from about 1200 ng/ml to about 1500 ng/ml when dosed at 15 mg to healthy volunteers.

12. The pharmaceutical composition according to claim 11, wherein the mean $C_{max}$ is from about 1215 ng/ml to about 1488 ng/ml when dosed at 15 mg to healthy volunteers.

13. The pharmaceutical composition according to claim 11 having a mean $AUC_{\infty}$ from about 39000 ng*hr/ml to about 61000 ng*hr/ml when dosed at 15 mg to healthy volunteers.

14. The pharmaceutical composition according to claim 11 having a mean $AUC_{\infty}$ from about 39082 ng*hr/ml to about 60588 ng*hr/ml when dosed at 15 mg to healthy volunteers.

15. The pharmaceutical composition according to claim 11 in the form of a tablet or capsule.

16. The pharmaceutical composition according to claim 11, wherein the meloxicam or salt thereof is present in an amount of about 5 mg to about 30 mg.

17. The pharmaceutical composition according to claim 11, further comprising at least one of lactose, cellulose, sodium citrate dihydrate, povidone, crospovidone, silicon dioxide, and magnesium stearate.

18. A pharmaceutical composition comprising particles of meloxicam or a salt thereof, wherein the particle size of meloxicam or a salt thereof is from about 4 microns to about 370 microns, $d_{(0.5)}$ is from about 20 microns to about 55 microns, and $d_{(0.9)}$ is less than about 90 microns;

between 60% and 85% by weight of meloxicam dissolves within about 15 minutes after starting dissolution of the pharmaceutical formulation when dissolved using an U.S.P. Dissolution Apparatus 2 (paddle apparatus) filled with a dissolution medium of 1000 ml of 0.01M $KH_2PO_4$ aqueous solution at a pH of about 7.5 at about 37° C. and a rotation speed of about 75 rpm; and the mean $C_{max}$ in the fasting state is from about 1200 ng/ml to about 1500 ng/ml when dosed at 15 mg to healthy volunteers.

19. The pharmaceutical formulation according to claim 18, further comprising lactose, cellulose, sodium citrate dihydrate, povidone, and crospovidone.

20. The pharmaceutical formulation according to claim 19, further comprising magnesium stearate.

21. The pharmaceutical formulation according to claim 18, wherein $d_{(0.5)}$ is about 32 microns and $d_{(0.9)}$ is about 57 microns.

* * * * *

UNITED STATES PATENT AND TRADEMARK OFFICE
CERTIFICATE OF CORRECTION

| | | |
|---|---|---|
| PATENT NO. | : 7,572,641 B2 | Page 1 of 1 |
| APPLICATION NO. | : 11/286184 | |
| DATED | : August 11, 2009 | |
| INVENTOR(S) | : Agami et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 612 days.

Signed and Sealed this

Seventh Day of September, 2010

David J. Kappos
*Director of the United States Patent and Trademark Office*